(12) United States Patent
Lee

(10) Patent No.: US 8,529,517 B2
(45) Date of Patent: Sep. 10, 2013

(54) AUTOFLUSH SYRINGE

(75) Inventor: Martin N. Lee, Sacramento, CA (US)

(73) Assignee: Shi Zi Technology, Ltd., Ebene (MU)

( * ) Notice: Subject to any disclaimer, the term of this patent is extended or adjusted under 35 U.S.C. 154(b) by 122 days.

(21) Appl. No.: 12/833,735

(22) Filed: Jul. 9, 2010

(65) Prior Publication Data
US 2010/0292672 A1    Nov. 18, 2010

Related U.S. Application Data

(63) Continuation of application No. 11/120,906, filed on May 2, 2005, now Pat. No. 8,075,533.

(51) Int. Cl.
*A61M 5/00* (2006.01)
*A61M 5/315* (2006.01)

(52) U.S. Cl.
USPC .......................................... 604/191; 604/220

(58) Field of Classification Search
USPC .............. 604/82–92, 191, 197, 198, 220, 231
See application file for complete search history.

(56) References Cited

U.S. PATENT DOCUMENTS

| | | |
|---|---|---|
| 368,627 A | 8/1887 | Threlfall |
| 553,234 A | 1/1896 | Finot |
| 1,142,682 A | 6/1915 | Dickinson |
| 1,234,582 A | 7/1917 | Trueblood |
| 1,343,787 A | 6/1920 | Neil |
| 2,841,145 A | 7/1958 | Epps |
| 3,487,834 A * | 1/1970 | Holbrook et al. ............. 604/117 |
| 3,559,645 A | 2/1971 | Schaller |
| 3,605,742 A | 9/1971 | Tibbs |
| 3,705,582 A | 12/1972 | Stumpf et al. |
| 3,729,031 A | 4/1973 | Baldwin |
| 3,747,812 A | 7/1973 | Karman et al. |
| 3,826,260 A * | 7/1974 | Killinger ...................... 604/413 |
| 3,835,835 A | 9/1974 | Thompson et al. |
| 3,923,058 A | 12/1975 | Weingarten |
| 4,171,698 A | 10/1979 | Genese |
| 4,188,949 A | 2/1980 | Antoshkiw |
| 4,313,439 A | 2/1982 | Babb et al. |
| 4,411,157 A | 10/1983 | Babin et al. |
| 4,425,120 A | 1/1984 | Sampson et al. |

(Continued)

FOREIGN PATENT DOCUMENTS

| | | |
|---|---|---|
| WO | WO 98/05433 | 2/1998 |
| WO | WO 2011/014259 | 2/2011 |
| WO | WO 2012/006555 | 1/2012 |

OTHER PUBLICATIONS

Lee et al.; U.S. Appl. No. 12/847,825 entitled Two chamber syringe with locking mechanism, filed Jul. 30, 2010.

*Primary Examiner* — Nicholas Lucchesi
*Assistant Examiner* — Nathan R Price
(74) *Attorney, Agent, or Firm* — Levine Bagade Han LLP

(57) ABSTRACT

A syringe includes a cartridge and a second chamber. The cartridge includes a first chamber, a first end having a conduit in liquid communication with the first chamber, a liquid disposed within the first chamber, a second end moveable within the first chamber, and a locking mechanism. The conduit is adapted and configured to rely on a property of the liquid to prevent movement of the liquid out of the first chamber. The locking mechanism is adapted to prevent movement of the second end within the first chamber while in the locked configuration. The cartridge is moveable within the second chamber.

13 Claims, 14 Drawing Sheets

(56) References Cited

U.S. PATENT DOCUMENTS

| | | | |
|---|---|---|---|
| 4,452,473 | A | 6/1984 | Ruschke |
| 4,476,866 | A | 10/1984 | Chin |
| 4,501,306 | A | 2/1985 | Chu et al. |
| 4,506,691 | A | 3/1985 | Tseo |
| 4,562,844 | A | 1/1986 | Carpenter et al. |
| 4,581,015 | A | 4/1986 | Alfano |
| 4,583,978 | A | 4/1986 | Porat et al. |
| 4,655,747 | A | 4/1987 | Allen, Jr. |
| 4,685,910 | A | 8/1987 | Schweizer |
| 4,693,706 | A | 9/1987 | Ennis, III |
| 4,702,737 | A | 10/1987 | Pizzino |
| 4,702,738 | A | 10/1987 | Spencer |
| 4,715,853 | A | 12/1987 | Prindle |
| 4,723,943 | A | 2/1988 | Spencer |
| 4,737,144 | A | 4/1988 | Choksi |
| 4,747,834 | A | 5/1988 | Prindle |
| 4,758,232 | A | 7/1988 | Chak |
| 4,871,353 | A | 10/1989 | Thomsen |
| 4,874,385 | A | 10/1989 | Moran et al. |
| 4,929,230 | A | 5/1990 | Pfleger |
| 4,929,238 | A | 5/1990 | Baum |
| 4,950,241 | A | 8/1990 | Ranford |
| 4,986,813 | A | 1/1991 | Blake, III et al. |
| 4,988,339 | A * | 1/1991 | Vadher .................... 604/197 |
| 4,994,045 | A | 2/1991 | Ranford |
| 5,032,117 | A | 7/1991 | Motta |
| 5,137,521 | A | 8/1992 | Wilkins |
| 5,176,635 | A * | 1/1993 | Dittmann .................... 604/87 |
| 5,358,497 | A | 10/1994 | Dorsey et al. |
| 5,374,250 | A | 12/1994 | Dixon |
| 5,435,076 | A | 7/1995 | Hjertman et al. |
| 5,496,284 | A | 3/1996 | Waldenburg |
| 5,512,054 | A | 4/1996 | Morningstar |
| 5,688,250 | A | 11/1997 | Naganuma |
| 5,713,873 | A | 2/1998 | Jehle |
| 5,720,731 | A | 2/1998 | Aramata et al. |
| 5,772,433 | A | 6/1998 | Esrock |
| 5,772,630 | A | 6/1998 | Ljungquist |
| 5,833,654 | A | 11/1998 | Powers et al. |
| 5,875,976 | A | 3/1999 | Nelson et al. |
| 6,090,077 | A | 7/2000 | Shaw |
| 6,093,170 | A | 7/2000 | Hsu et al. |
| 6,270,482 | B1 | 8/2001 | Rosoff et al. |
| 6,361,524 | B1 | 3/2002 | Odell et al. |
| 6,423,050 | B1 | 7/2002 | Twardowski |
| 6,558,358 | B2 | 5/2003 | Rosoff et al. |
| 6,719,733 | B1 | 4/2004 | Heffernan et al. |
| 6,723,074 | B1 | 4/2004 | Halseth |
| 6,780,167 | B2 | 8/2004 | Leone |
| 6,866,653 | B2 | 3/2005 | Bae |
| 6,873,627 | B1 | 3/2005 | Miller et al. |
| 6,972,005 | B2 | 12/2005 | Boehm, Jr. et al. |
| 6,997,910 | B2 | 2/2006 | Howlett et al. |
| 7,011,650 | B2 | 3/2006 | Rosoff et al. |
| 7,041,084 | B2 | 5/2006 | Fojtik |
| 7,048,720 | B1 | 5/2006 | Thorne, Jr. et al. |
| 7,101,354 | B2 | 9/2006 | Thorne, Jr. et al. |
| 7,204,797 | B2 | 4/2007 | Reilly et al. |
| 8,075,533 | B2 | 12/2011 | Lee |
| 8,075,547 | B2 | 12/2011 | Lee |
| 2002/0022807 | A1 | 2/2002 | Duchon et al. |
| 2002/0035351 | A1 | 3/2002 | Lodice |
| 2002/0128609 | A1 | 9/2002 | Koch et al. |
| 2002/0197211 | A1 | 12/2002 | Henriksen et al. |
| 2003/0009132 | A1 | 1/2003 | Schwartz et al. |
| 2003/0040712 | A1 | 2/2003 | Ray et al. |
| 2003/0199816 | A1 | 10/2003 | Ramming |
| 2003/0212371 | A1 | 11/2003 | Smith et al. |
| 2003/0213504 | A1 | 11/2003 | Cerra et al. |
| 2004/0039346 | A1 | 2/2004 | Baldwin et al. |
| 2004/0097875 | A1 | 5/2004 | Bae |
| 2004/0116871 | A1 | 6/2004 | Vincent |
| 2005/0065479 | A1 | 3/2005 | Schiller et al. |
| 2005/0081914 | A1 | 4/2005 | Kalley et al. |
| 2005/0094556 | A1 | 5/2005 | Thompson et al. |
| 2006/0030816 | A1 | 2/2006 | Zubry |
| 2006/0100591 | A1 | 5/2006 | Alheidt et al. |
| 2006/0173415 | A1 | 8/2006 | Cummins |
| 2006/0178644 | A1 | 8/2006 | Reynolds |
| 2006/0256815 | A1 | 11/2006 | Kivinen et al. |
| 2006/0258977 | A1 | 11/2006 | Lee |
| 2007/0088283 | A1 | 4/2007 | Hongo et al. |
| 2007/0249996 | A1 | 10/2007 | Tennican et al. |
| 2007/0265574 | A1 | 11/2007 | Tennican et al. |
| 2008/0114304 | A1 | 5/2008 | Nalesso et al. |
| 2008/0119782 | A1 | 5/2008 | Steinman et al. |
| 2008/0119794 | A1 | 5/2008 | Alheidt et al. |
| 2009/0287184 | A1 | 11/2009 | Lee |
| 2010/0292672 | A1 | 11/2010 | Lee |
| 2012/0029471 | A1 | 2/2012 | Lee et al. |
| 2012/0197232 | A1 | 8/2012 | Lee et al. |

* cited by examiner

FIG. 1
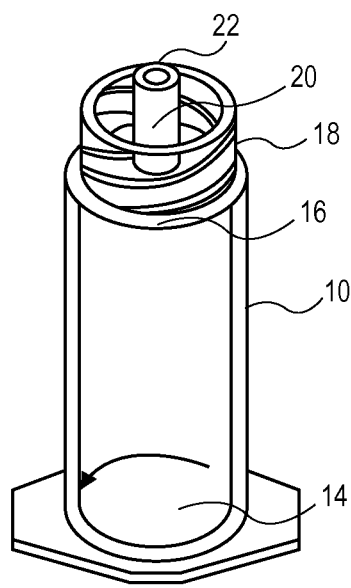
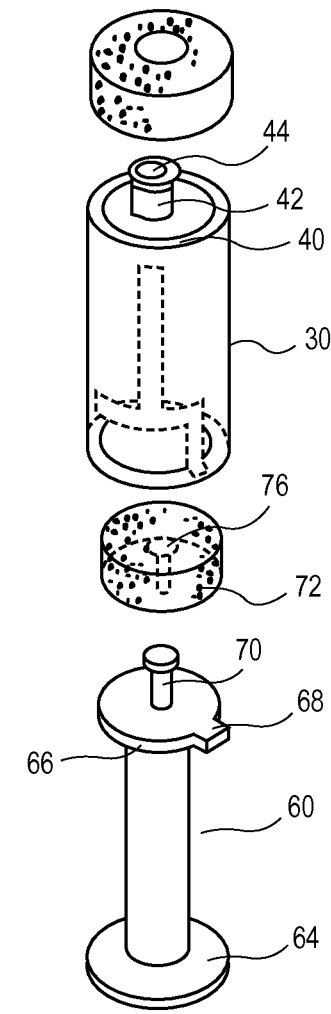

FIG. 2
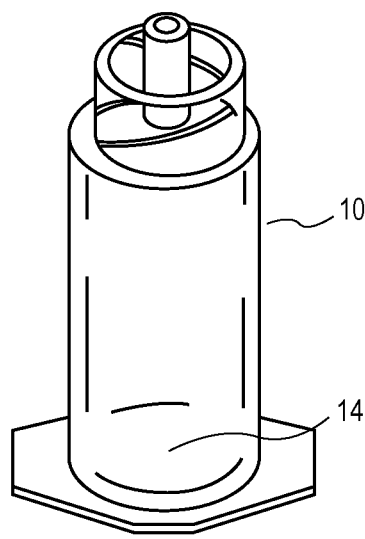
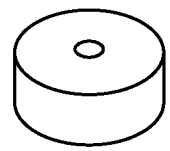
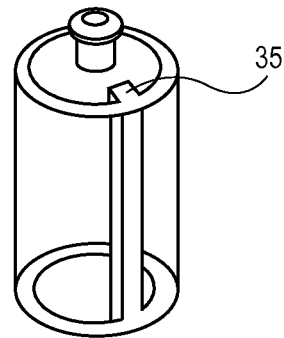
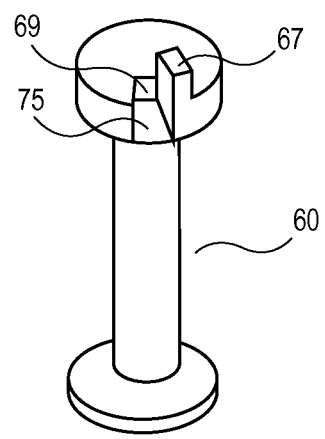

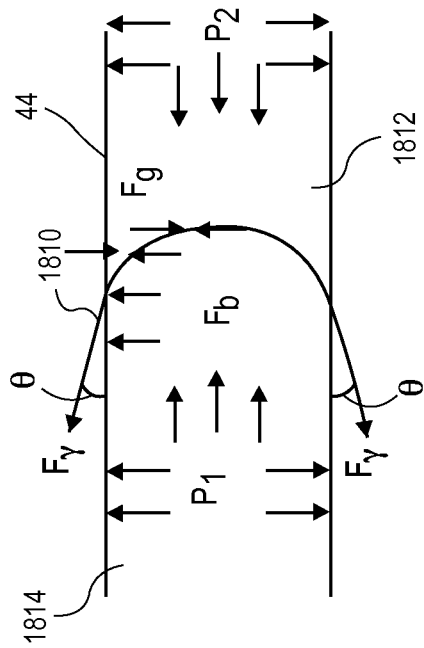
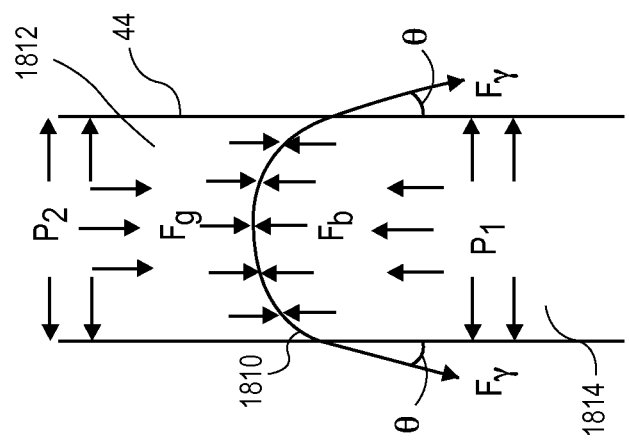
FIG. 18A
FIG. 18B

AUTOFLUSH SYRINGE

CROSS-REFERENCE TO RELATED APPLICATIONS

This application is a Continuation-in-part of pending U.S. application Ser. No. 11/120,906, filed May 2, 2005, now U.S. Pat. No. 8,075,533 entitled "Autoflush Syringe", which is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

1. Field of the Invention

This invention relates to syringe injectors.

2. General Background

Syringes are commonly used in the medical field for the injection or withdrawal of liquid medications. Syringes typically have a hollow glass or plastic barrel with an internal piston. By moving the piston, a user can create a positive or negative pressure inside the barrel, thereby transmitting fluid out of or into the barrel through a small opening opposite the piston.

Syringes are often used in intravenous therapy where the syringe may directly puncture the vein, or more commonly, may be used in conjunction with a catheter. When a catheter is used, one side of the catheter remains in the vein, while the other side remains outside the skin. The external portion of the catheter typically includes a coupler for connection to a syringe.

After injection in either procedure, a small amount of medication is typically left behind. When a syringe is used, the medication remains within the tip of the syringe. When a catheter is used in conjunction with a syringe, the unadministered medication remains in both the tip of the syringe and in the catheter.

This leftover medication is problematic for several reasons. First, it necessarily means that the entire amount of medicine drawn into the syringe does not reach the patient. Second, many medications are time sensitive and should not remain in the catheter until a subsequent medicine flushes it through.

In a catheter system, these problems are solved using a second liquid to immediately flush the remaining medication out of the catheter and into the patient. Generally, a second syringe prefilled with a flushing solution provides the second liquid.

While many different liquids may be used to flush the catheter, the most commonly used liquid is a 0.9% concentration of sodium chloride (saline solution). The saline solution is injected from a syringe into the catheter, thereby flushing any stranded medication into the patient. Thus, the saline flush ensures that a full dosage of medication has been timely delivered.

This method for purging the catheter has certain disadvantages. For instance, by using a separate syringe for each injection, there is an increased chance of medical error. Most medicines are colorless (like the saline solution), and it is easy to accidentally administer medication when intending to flush the line or vice versa. This risk is increased when clinicians carry medicines for multiple patients at one time.

The likelihood of error is compounded in an emergency, when it may be necessary to inject several medications quickly and in a specific order. In such situations, a separate saline flush is necessary between every individual medication injection, so the risk of error is high, and the consequences of a mistake may be grave.

Finally, the clinician may be distracted by a separate medical need during the time between the injection of medication and the saline flush. Without some reminder, the clinician may forget that he or she has not flushed the line.

Even if all precautions are taken and the two injections are made in the proper order, drawbacks remain. With each breach of the catheter's seal for injection, the patient is potentially exposed to bacteria, increasing the risk of infection. By requiring a clinician to access the system once for the medication and a second time for the flush, the risk of infection is doubled.

Using a second syringe for the saline flush also wastes resources. Attaching a second syringe to the catheter takes time, and since a clinician may perform a saline flush more than one hundred times per day, this lost time adds up quickly. Finally, requiring a second syringe unnecessarily increases the already significant costs related to manufacturing, shipping, storage, and disposal of syringes.

Syringes adapted to deliver multiple fluids for sequential injection have been described in the prior art. However, due to design limitations, no syringe has become widely accepted that allows routine medication administration and subsequent catheter flushing from a single syringe. Some prior art syringes include a "standard" syringe that is separated by an intermediate sliding stopper into two chambers. The sliding stopper receives motive force communicated through an intermediate fluid from a primary stopper (part of a plunger assembly of the standard syringe) against which an external force is applied. Examples of such prior art devices may be found in U.S. Pat. Nos. 5,720,731, 6,997,910 and 7,101,354, which describe multiple embodiments of a conventional syringe adapted to deliver multiple fluids and a displaceable valved stopper which partitions a conventional syringe. Other sequential delivery syringes have been developed, such as U.S. Pat. No. 6,723,074, which uses a piercing member to open an internal chamber.

The previously described syringes adapted to deliver multiple fluids have not been widely adopted because they generally require the delivery of two fluids that are both prefilled during manufacturing. Rather, current standard practice is to use two separate syringes—one prefilled with saline and one empty syringe that is filled with medication shortly before administration. Requiring hospitals to change their practice to using previously described multi-fluid syringes is unfeasible because the hospitals would be required to keep an unreasonable number of prefilled medicine syringes in stock to accommodate the varied number of doses and types of medications required for routine patient care. The applicant's invention solves all of these problems, and does so with a simple design that makes storage easy and keeps manufacturing costs to a minimum. The present invention includes all the functionality of a standard syringe (including the ability to depress and pull back on the plunger when withdrawing medicines from a multidose vial) independent of the flush chamber. The design of the syringe takes advantage of basic fluid mechanics to keep the flush and the medicine from contacting each other during use. The present invention advances the state of the art by providing a cost-effective single syringe that both administers medication and flushes the intravenous system. By using a single syringe for both purposes, a clinician need only access the intravenous catheter once, thereby decreasing the rate of error and infection. Additionally, the presence of the saline or other solution in the syringe after injection alerts the clinician of the need to flush the system, thus reducing the chance that the flush would be forgotten. Finally, the extra cost and time associated with a second "flush-only" syringe would be eliminated.

SUMMARY OF THE INVENTION

The present invention is a two-chambered syringe with an outer barrel having an open end for slidably receiving an inner barrel/first piston. A second piston is slidably movable in the inner barrel/first piston. A latching mechanism locks and unlocks the inner barrel/first piston to the second piston. In the locked configuration, the second piston is prevented from substantially all longitudinal movement relative to the inner barrel/first piston, and in the unlocked configuration, the second piston may move longitudinally within the inner barrel. The invention may be used, for example, to administer a medicine from the outer barrel and then administer a flushing solution from the inner barrel. Thus, the invention may be used as a traditional syringe to withdraw medicine from a bottle, either before or after the administration of a second flushing solution contained in the syringe.

A cost-effective single syringe that both administers medication and flushes the intravenous system is needed to improve the standard of care. It is desirable to allow caregivers to follow their standard syringe filling procedures; to not rely on the fluid in the distal chamber to expel the primary fluid (medicine) from the syringe; to include a physical locking mechanism such that the intermediate fluid cannot be expelled accidentally while depressing the plunger during routine filling; to utilize basic fluid mechanics to keep the two fluids separate when disposed within the syringe; and to not limit the volume of medicine that can be filled into the proximal chamber.

Described herein are syringe devices, systems and methods. In general, a syringe includes a cartridge and a second chamber. The cartridge includes a first chamber, a first end having a conduit in liquid communication with the first chamber, a liquid disposed within the first chamber, a second end moveable within the first chamber, and a locking mechanism. The conduit is adapted and configured to rely on a property of the liquid to prevent movement of the liquid out of the first chamber. The locking mechanism is adapted to prevent movement of the second end within the first chamber while in the locked configuration. The cartridge is moveable within the second chamber.

This and other embodiments can include one or more of the following features. The conduit can be adapted and configured to rely on a property of the liquid to cause a liquid-air interface to form in the conduit that prevents movement of the liquid out of the first chamber. The syringe can further include a second liquid disposed within the second chamber. The conduit can be further adapted and configured to rely on a property of the second liquid to prevent movement of the second liquid into the first chamber. The syringe can further include a gas bubble disposed in the conduit between the first liquid and the second liquid. The gas bubble can have a volume that can readily dissolve into solution when injected into a patient. The cartridge can include about 1 to 10 ml of liquid disposed within the first chamber, such as 2 to 3 ml. The volume of the first chamber can be constant while the locking mechanism is in the locked configuration. The conduit can include a surface finish that contributes to preventing movement of the liquid out of the first chamber. The dimensions of the conduit can contribute to preventing movement of the liquid out of the first chamber. The conduit can have a diameter of about 0.069 inches. The conduit can have a length of about 0.4 inches. The second end of the cartridge can further include a handle sized and configured to move the second end within the first chamber when the locking mechanism is in the unlocked configuration. The handle can be configured to move the cartridge within the second chamber when the locking mechanism is in the locked configuration.

In general, a method of filling a syringe cartridge includes: injecting a liquid into a syringe having a cartridge, the cartridge including a first chamber and a conduit connected to the first chamber, wherein the liquid is injected into the first chamber through the conduit; and using the configuration of the conduit and the properties of the liquid to prevent movement of the liquid out of the conduit.

This and other embodiments may include one or more of the following features. Using the configuration of the conduit and the properties of the liquid to prevent movement of the liquid out of the conduit can include creating a liquid-air interface within the conduit. The method can further include the step of placing the cartridge within a second chamber of the syringe, wherein the cartridge is movable within the second chamber. The injecting step can further include injecting the liquid into the first chamber through the conduit and through an outlet of a second chamber of the syringe, wherein the cartridge is movable within the second chamber. The injecting step can further include injecting a liquid into the cartridge chamber with a needle positioned within the conduit of the cartridge.

In general, a method of using a syringe having a cartridge, wherein the cartridge includes a first chamber, a first end that defines a conduit in liquid communication with the first chamber, and a first liquid disposed within the first chamber, wherein the conduit is adapted and configured to rely on a property of the first liquid to prevent movement of the first liquid out of the first chamber, and wherein the syringe further includes a second chamber having an outlet, the cartridge movable within the second chamber, includes: drawing a second liquid into the second chamber through the outlet of the second chamber by moving the cartridge within the first chamber, wherein the conduit is further adapted and configured to rely on a property of the second liquid to prevent movement of the second liquid into the first chamber.

This and other embodiments may include one or more of the following features. The second liquid can be drawn from a bottle, and the method can further include injecting air from the second chamber into the bottle prior to drawing the second liquid into the second chamber. The method can further include forming a gas bubble between the first and second liquids. The method can further include: expelling the second liquid from the first chamber through the outlet by moving the cartridge within the second chamber towards the outlet; releasing a locking mechanism from a locked configuration to an unlocked configuration to allow movement of a second end of the cartridge within the first chamber; and expelling the first liquid from the first chamber through the outlet by moving the second end of the cartridge within the first chamber towards the conduit. The expelling the first liquid step can further include expelling a gas bubble from the conduit through the outlet. The releasing step can further include rotating a second end of the cartridge with respect to the first chamber to release the locking mechanism.

BRIEF DESCRIPTION OF THE DRAWINGS

FIG. 1 is an exploded perspective view of a two-chambered syringe according to an embodiment of the present invention.

FIG. 2 is an exploded perspective view of a two-chambered syringe according to an embodiment of the present invention.

FIG. 15(a) depicts the syringe as delivered to the clinician. FIG. 15(b) depicts the second chamber being filled with air. FIG. 15(c) depicts the air being injected into a medicine bottle. FIG. 15(d) depicts the withdrawal of medicine from a bottle into the second chamber. FIG. 15(e) depicts the administration of the medicine to a patient. FIG. 15(f) depicts unlocking the second chamber from the back chamber. FIG. 15(f) depicts the administration of the prefilled flush solution.

FIGS. 18A and B represent the balance of forces inside a conduit of a syringe.

DETAILED DESCRIPTION OF THE INVENTION

Figure 3:
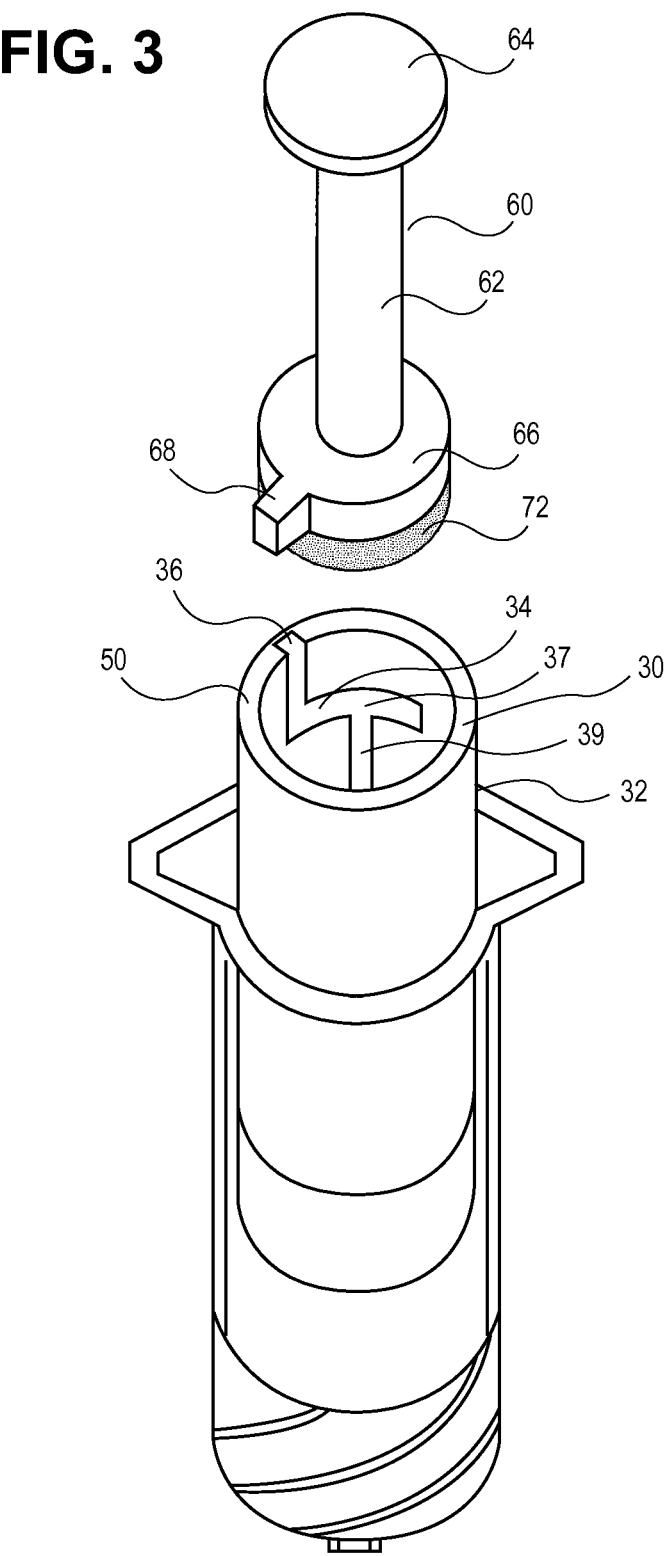
FIG. 3 is a perspective view of the embodiment depicted in FIG. 1.

Described herein are syringe devices, systems and methods. In general, the syringe may include a second chamber and a cartridge movable within the second chamber. The cartridge includes a cartridge chamber, a first end that defines a conduit in fluid communication with the cartridge chamber and the second chamber, a liquid disposed within the cartridge chamber (first chamber) such that there is a liquid-air interface at or within the conduit, wherein the liquid has a fluid property such that the liquid-air interface, cooperating with the conduit and the fixed volume of the cartridge, prevents movement of the liquid out of the conduit, a second end, movable within the cartridge chamber, and a locking mechanism having a locked configuration and an unlocked configuration, the locking mechanism preventing movement of the second end within the cartridge chamber while in the locked configuration. In general, the methods of filling a syringe during manufacturing may include the steps of injecting a liquid into a cartridge chamber through a conduit of the cartridge and creating a liquid-air interface within the conduit, wherein the liquid-air interface, cooperating with the conduit, prevents movement of the liquid out of the conduit. In general, the methods of using a syringe may include the steps of drawing a second liquid into the second chamber through the proximal outlet by moving the cartridge distally within the first chamber and creating a second liquid-air interface within the conduit, wherein the second liquid-air interface, cooperating with the conduit and locked prefilled cartridge, prevents movement of the first liquid out of the conduit.

The syringe devices, systems, methods, and any combination thereof described herein provide at least the following advantages. First, the syringe described herein does not rely on an intermediate fluid in the distal chamber to expel the primary fluid (medicine) from the syringe. Not using an intermediate fluid to expel the primary fluid avoids mixture that can occur between the two fluids when the syringe is used in standard fashion. Ensuring that the two fluids are not mixed ensures that the patient receives the correct fluids during treatment. As a result, the syringe is more versatile and reliable.

Further, the syringe cartridge includes a conduit designed to keep two fluids in a multi-chamber syringe separate from one another. Keeping the two fluids separate from one another avoids mixing of the two fluids. As noted above, avoiding mixing ensures that the patient receives the correct fluid during treatment, making the syringe more versatile and reliable.

Moreover, prefilled saline flush cannot be inadvertently expelled during routine use. This is an advantage, because, when using a syringe, a caretaker will typically eject air from the proximal chamber prior to drawing a medicine into the proximal chamber, as described above. In pushing the air from the proximal chamber in a prior art syringe lacking a locking mechanism, the caretaker could easily cause the plunger to contact the proximal end of the syringe barrel which would prematurely open the valve, thereby accidentally expelling the flushing liquid. Accidental expelling of the intermediate fluid can cause mixing of the two fluids in the syringe. A physical locking mechanism in conjunction with the other syringe features, as described herein, will therefore keep the fluids from mixing even in similar stresses and situations. As discussed above, avoiding mixing ensures that the syringe is more versatile and reliable.

Additionally, the syringe described herein provides the advantage that it allows the filling of the distal chamber from the proximal end during manufacturing. Filling the distal chamber from the proximal end during manufacturing enables complete filling of the distal chamber without trapping any large/non injectable air bubbles. Some prior art syringes that are adapted to deliver multiple fluids require filling procedures that include placing an intermediate sliding stopper into a conventional syringe barrel, then filling the distal chamber from the distal end with a liquid, such as saline, and subsequently installing the plunger assembly. By filling the distal chamber with saline before installing the conventional syringe plunger, the prior art syringe has the disadvantage of reliance on the compressibility of the gas trapped in the distal chamber for a successful installation of the plunger. Therefore, by allowing the filling of the distal chamber without trapping large air bubbles, the syringe described herein can provide more accurate and reliable administration. Further, filling the distal chamber from during manufacturing gives the caretaker the ability to fill the proximal chamber with a necessary amount of medicine at the time of administration. Some prior art syringes that are adapted to deliver multiple fluids require that they be provided to a caregiver with prefilled distal (saline) and proximal (medicine) chambers. Such a requirement is not desirable, as many patients require different doses of the same medication. If hospitals were to adopt the use of syringes prefilled with medication, it would cause a tremendous storage and utilization problem. Thus, giving the caretaker the ability to fill the proximal chamber with a necessary amount of medicine at the time of administration advantageously allows patients to receive varying amounts of medications.

Additionally, the syringe described herein allows caregivers to follow their standard syringe filling procedures. The most common procedure a clinician uses to fill an empty syringe with medication includes the steps of (1) fitting a syringe with a needle (metal or plastic) to penetrate the seal on a medicine bottle; (2) pulling the handle of the syringe back (distally) to draw air into the syringe of equal or greater volume than the medicine that is to be withdrawn; (3) inserting the air filled syringe with attached needle into the medicine bottle; (4) depressing (pushing proximally) the plunger to inject the air into the medicine bottle; (5) pulling the handle of the syringe back (distally) to draw medicine from the bottle into the syringe; and (6) withdrawing the needle/syringe from the medicine bottle and removing the needle from the syringe. Prior syringes that are adapted to deliver multiple fluids cannot be used in this procedure for at least the reason that during Step 4, after injecting all the air from the proximal chamber of the syringe into the medicine bottle, the plunger will often collide with the internal surface of the inside of the syringe barrel. This collision causes the displaceable valved stopper to open and remain open. Once the valve is open, pulling back on the plunger would cause medicine to flow through the open valve and mix with the contents of distal chamber. Alternatively, if the forward force were continually applied, after the valve was opened, the contents of the distal chamber would flow through the open valve into the medicine bottle. Neither one of these scenarios is acceptable. The syringe described herein, including a physical locking mechanism and separate cartridge (including an inner barrel) which is adapted to use fluid mechanics to keep fluids separate, is ideally suited for a caregiver's standard filling procedure.

A further advantage of the syringe described herein is that it does not limit the volume of medicine that can be filled into the proximal chamber. A disadvantage of some prior syringes that are adapted to deliver multiple fluids by sectioning a standard syringe into two compartments is that the volume of medicine that can be filled into the proximal chamber is limited by the presence of the distal chamber. In general the greater the diameter of the syringe barrel, the less exact a measurement of volume can be made by reading the fluid meniscus against gradations marked on the outside of the syringe. The accuracy required is generally related the total volume of medicine to be administered, the smaller the dose of medicine the more accurate measurement is needed. To solve this problem clinicians use a wide range of syringe sizes depending on the amount of medication to be administered. Syringes from 1 ml to 60 ml are the most commonly used sizes. In the prior art syringes that are adapted to deliver multiple fluids the distal chamber defined by the sliding stopper takes up space within the standard syringe barrel (the effective volume for medication is decreased by the distal chamber volume by about a factor of 2 for a given syringe size) and therefore clinicians would have to use a relatively larger syringe barrel size and therefore less accurate measurements to attempt to administer the same volume of medicine. The syringe described herein includes a separate cartridge that includes the distal chamber, and therefore does not negatively impact the potential size of the proximal chamber and its capability to hold a volume of medicine.

Figure 4:
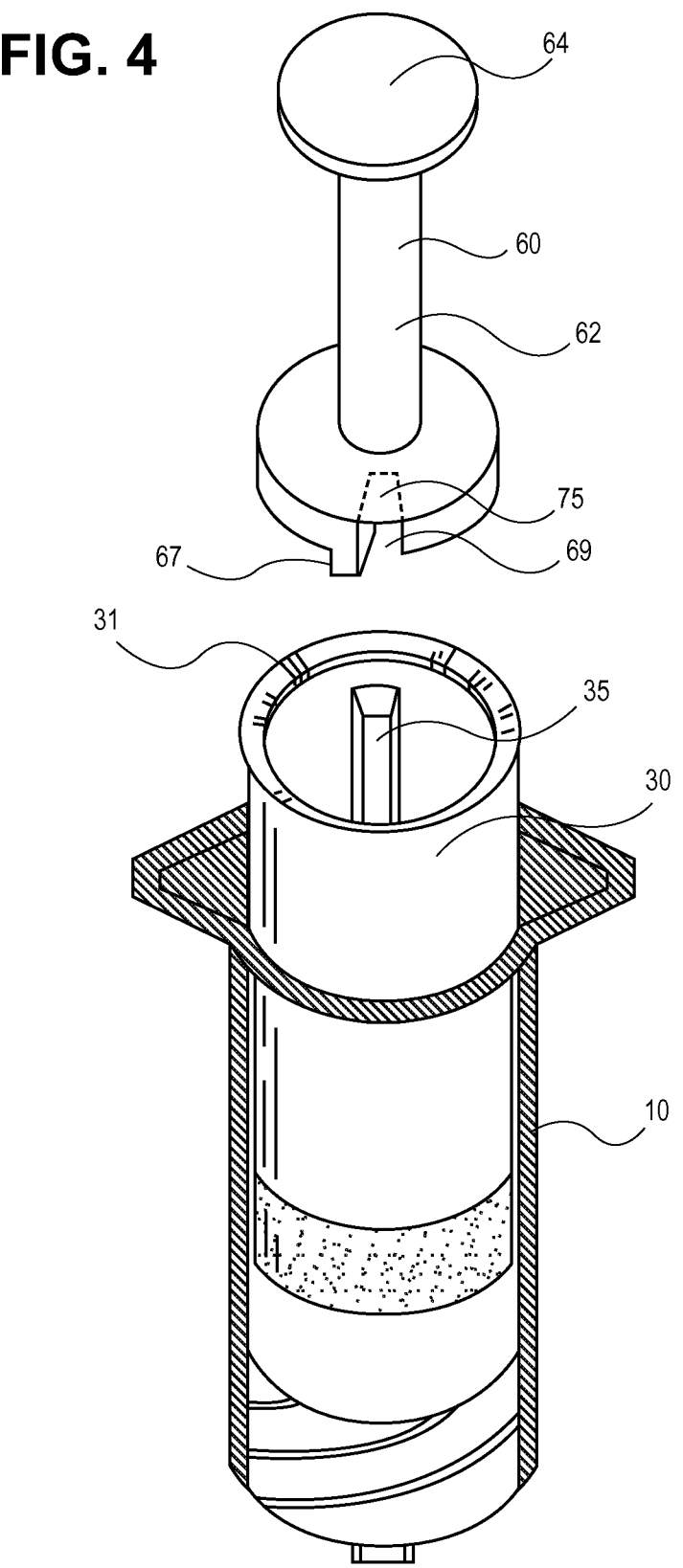
FIG. 4 is a perspective view of the embodiment depicted in FIG. 2.
Figure 5:
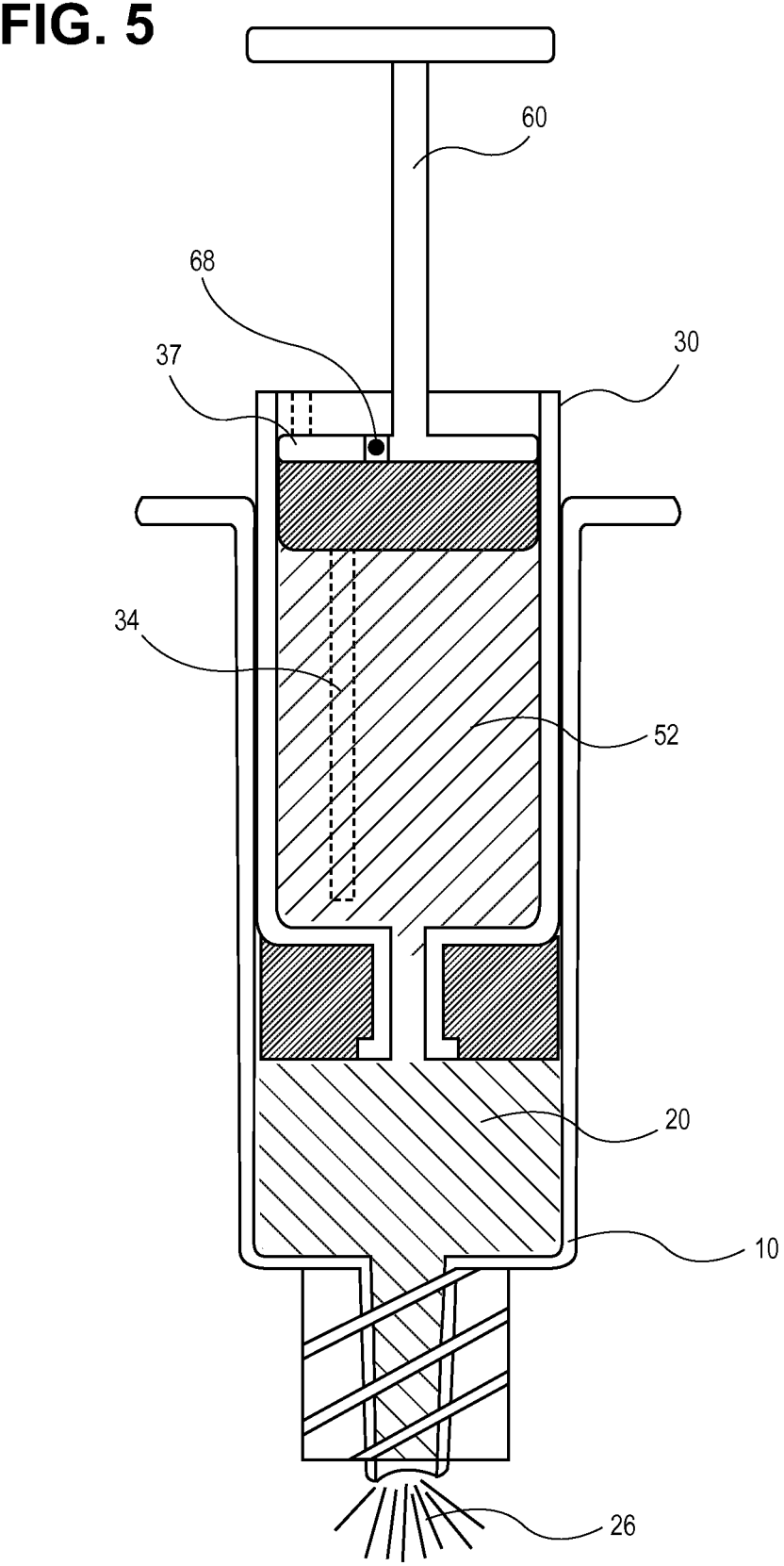
FIG. 5 is a side cross-sectional view of the embodiment depicted in FIG. 1, with the inner barrel/first piston full of a liquid such as a saline solution.

The present invention is a two-chambered syringe with three basic components: (i) an outer barrel 10 for holding a liquid 20, (ii) an inner barrel/first piston 30 for holding a flushing liquid 52, and (iii) a second piston 60. See FIG. 5. The syringe also includes a latching mechanism for controlling the movement of the second piston 60 in the inner barrel/first piston 30. See FIGS. 3 and 4.

Figure 6:
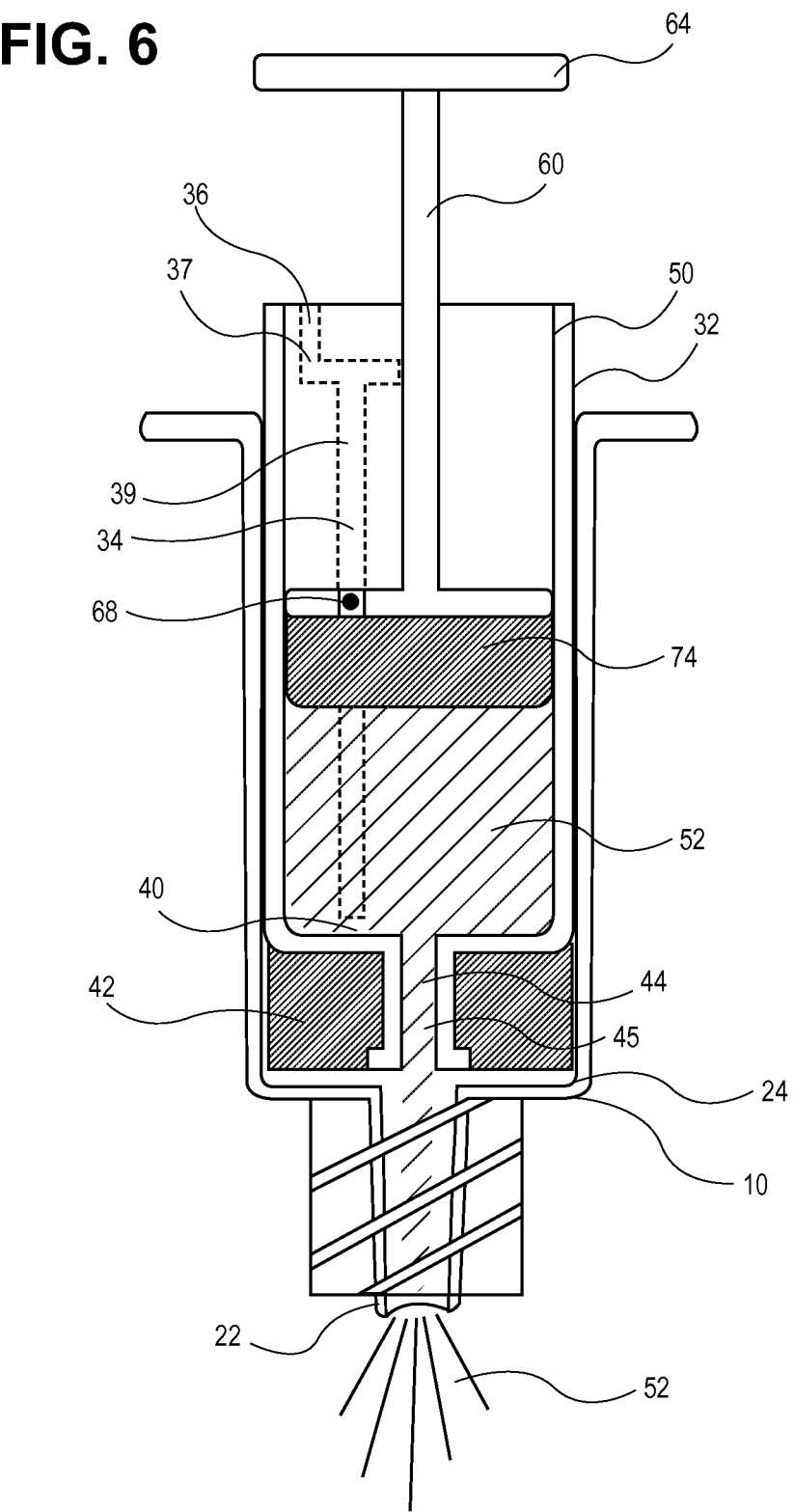
FIG. 6 is a side cross-sectional view of the embodiment depicted in FIG. 1, with the second piston partially depressed, thereby expelling some of the liquid.

The barrels and pistons may be constructed of polypropylene or other similar inert, nonreactive semi-flexible material. Both barrels 10, 30 are generally circular cylinders. The inner barrel/first piston 30 acts as both a barrel and a piston. That is, it both holds liquid like a barrel, and may be used as a plunger to expel liquid from the outer barrel 10. See FIGS. 5 and 6.

For purposes of this patent, the proximal end of the syringe is the end typically comprising a first conduit 20, while the distal end is the end of the syringe typically comprising the second piston 60 and a gripping handle 64. See FIGS. 1 and 2.

The outer barrel 10 has an outer barrel distal open end 14 adapted for receiving the inner barrel/first piston 30. See FIG. 1. The inner barrel/first piston 30 is slidably contained in outer barrel 10 in a liquid-tight relation, similar to the piston or plunger in syringes common to the art. See FIGS. 1-6 and 15.

In one embodiment, a proximal end 16 of the outer barrel 10 may comprise an adapter 18, such as a luer connector device as disclosed in U.S. Pat. No. 4,452,473 or other locking means common in the art. See FIG. 1. The adapter 18 allows a connection between the present invention and an intravenous system. An outer barrel open proximal end 22 is at the proximal end 16 of the outer barrel 10 and may contain a first conduit 20. See FIG. 1. The distal end of first conduit 20 is in communication with the proximal end 16 of the outer barrel 10, providing a passageway for fluid from either the outer barrel 10 or the inner barrel/first piston 30. See FIG. 1.

Figure 7:
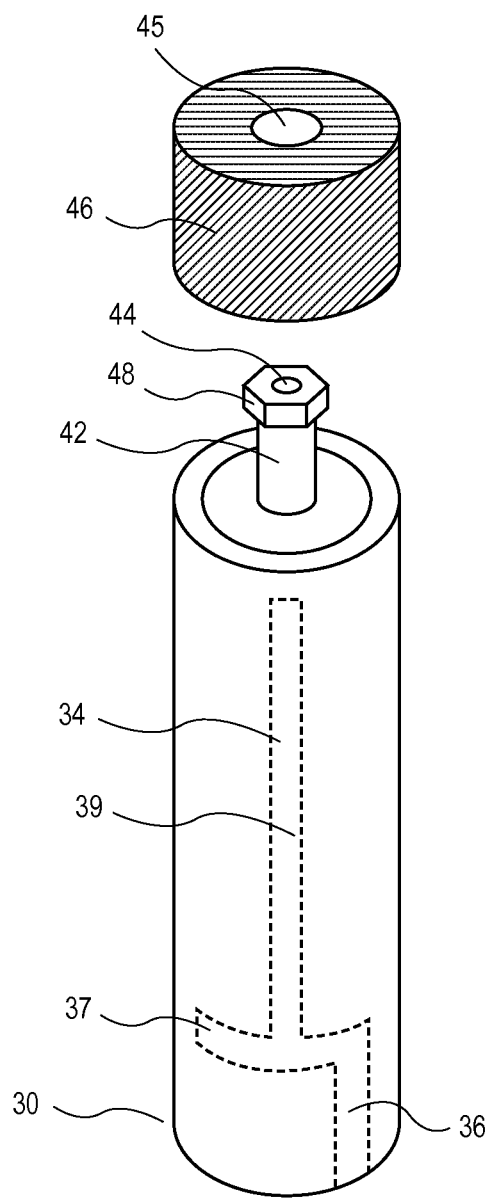
FIG. 7 is a perspective view of the inner barrel/first piston and sealing ring depicted in FIG. 1.
Figure 8:
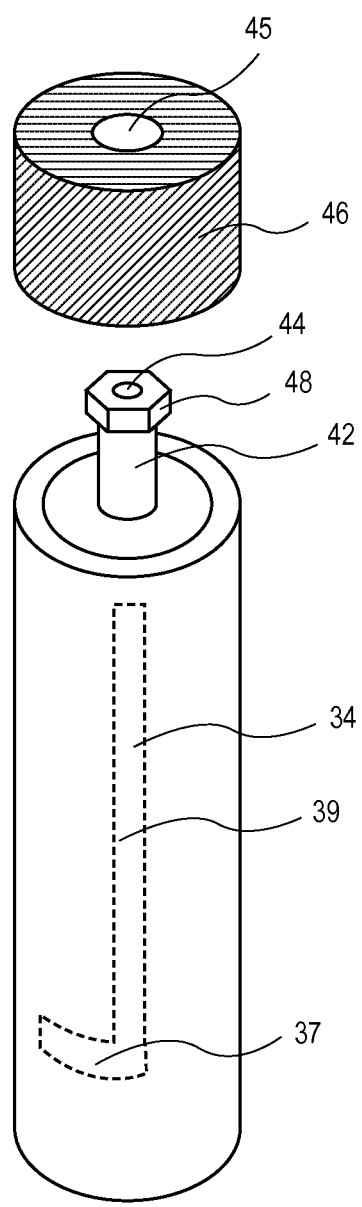
FIG. 8 is a perspective view of the inner barrel/first piston and sealing ring according to an alternative embodiment of the present invention.
Figure 9:
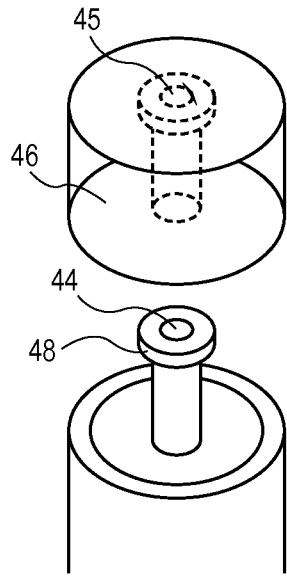
FIGS. 9-14 are perspective views of the proximal end of the second piston and sealing ring according to alternative embodiments of the present invention.
Figure 10:
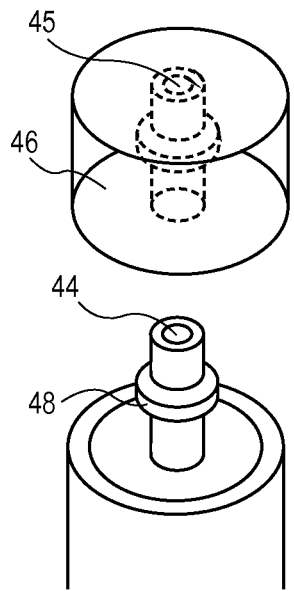
Figure 11:
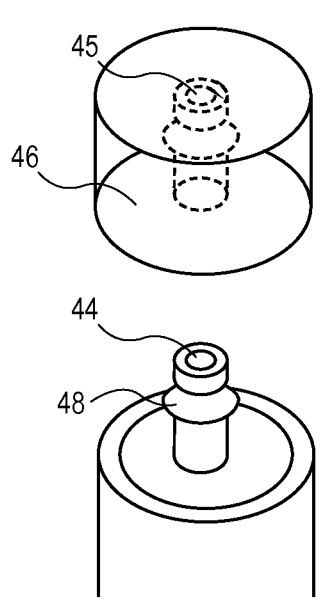
Figure 12:
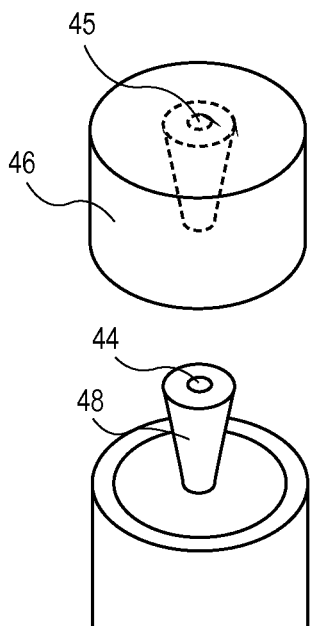
Figure 13:
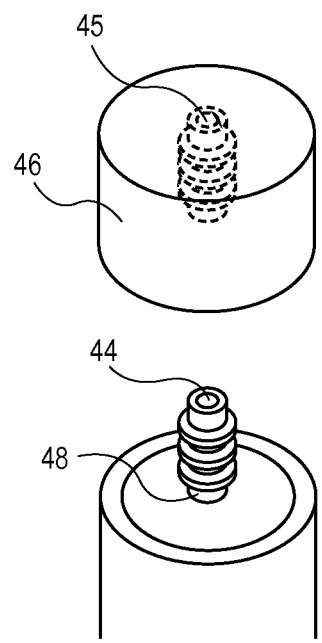
Figure 14:
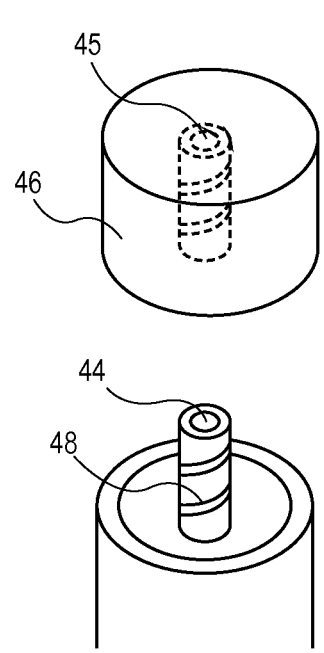
Figure 15:
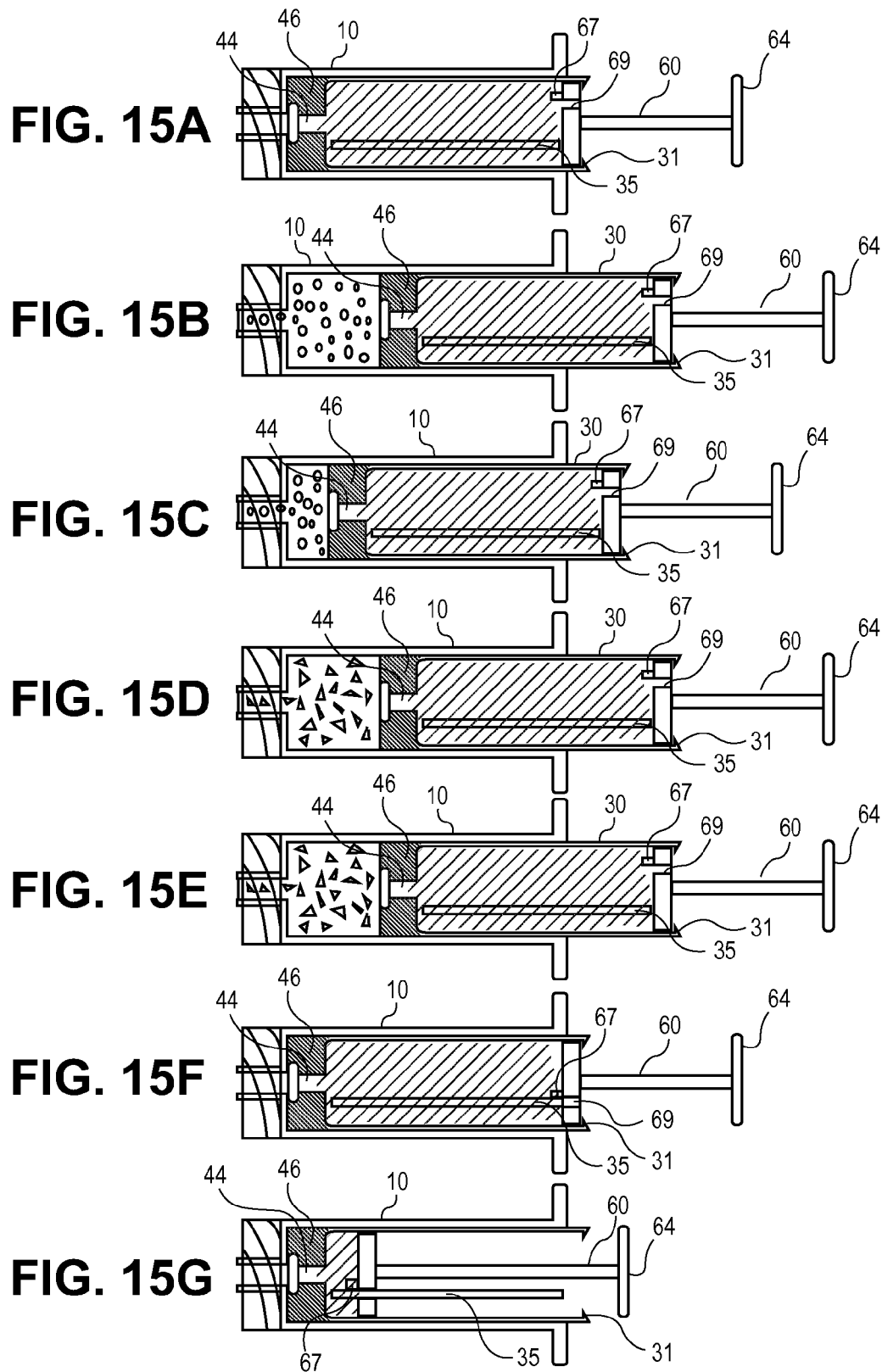
FIGS. 15(a)-(g) are side cross-sectional views of various stages of operation of the two-chambered syringe depicted in FIG. 1.
Figure 16:
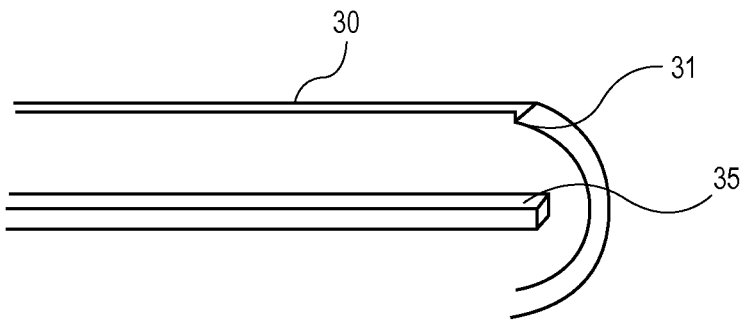
FIG. 16 is a perspective cut away view of the inner barrel/first piston showing the raised track and rear lip.

The inner barrel/first piston 30 has an inner barrel/first piston proximal end 40 slidably received within the outer barrel open distal end 14. See FIG. 1. It also includes a hollow projection 42 that extends proximally out of the inner barrel/first piston 30. See FIGS. 1, 9-14. The hollow projection 42 defines a second conduit 44 through which liquid flows from the inner barrel/first piston 30 to the outer barrel 10. See FIGS. 1 and 6-8. The hollow projection 42 has a flared tip 48 that secures a first sealing ring 46, as shown in FIGS. 7 and 8. The flared tip 48 may take many different forms, as shown in FIGS. 9-14.

The first sealing ring 46 comprises a sealing ring conduit 45 through which extends the hollow projection 42. See FIGS. 7-14. The first sealing ring 46 is substantially the same diameter as both the inner barrel/first piston outer wall 32 and the outer barrel inner wall 24, creating a liquid tight seal between the inner barrel/first piston 30 and the outer barrel 10. See FIG. 6. Thus, the only fluid connection between the inner barrel/first piston 30 and the outer barrel 10 is through the second conduit 44 and the sealing ring conduit 45. The sealing ring 46 may be constructed of an elastic material such as natural or synthetic rubber.

The flushing liquid 52 is inside the inner barrel/first piston 30. See FIGS. 5, 5-6. The flushing liquid 52 may be a saline solution, or any other suitable solution, such as heparin, when anticoagulation is desired, or antibiotics, when a line infection is being treated.

The flushing liquid 52 occupies substantially all of the space defined by the inner barrel/first piston inner wall 50, and initially extends partially through the second conduit 44 defined by the hollow projection 42. See FIG. 6. Because the flushing liquid 52 only extends partially through the second conduit 44, the flushing liquid 52 remains isolated from any liquid later drawn into the outer barrel 10.

Figure 17A:
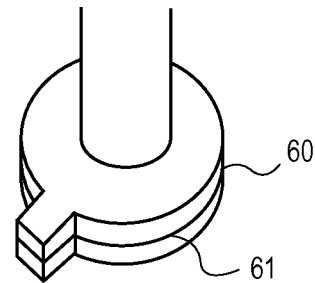
FIGS. 17(a) and (b) are perspective views of a portion of the inner barrel of a two-chambered syringe according to an embodiment of the present invention.
Figure 17B:
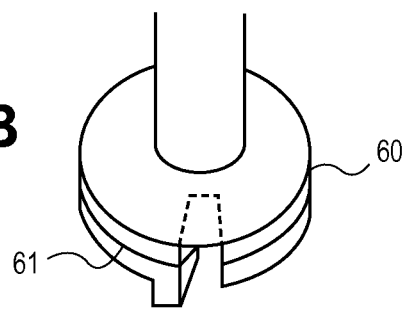

The second piston 60 is slidably placed within the inner barrel/first piston 30. See FIGS. 3-5 and 15. The second piston 60 comprises a second piston proximal end 66 further comprising a solid projection 70 that fits through an aperture 76 in a second sealing ring 72, thereby attaching the second piston 60 to the second sealing ring 72. See FIGS. 1, 3. The second sealing ring 72 is of substantially equal diameter to the inner barrel/first piston inner wall 50, and is created from an elastic rubber-like material that provides a liquid-tight seal for the inner barrel/first piston 30. See FIG. 3. Alternatively, this liquid-tight seal may be created by a similar rubber-like sealing material 61 placed around the periphery of the proximal end of the second piston 60. See FIG. 17. The second piston 60 moves in and out of the lumen of inner barrel/first piston 30, thereby dispensing liquid from or drawing liquid into the inner barrel/first piston 30. See FIG. 3.

Extending distally from second piston proximal end 66 is a piston rod 62. See FIGS. 3 and 4. A gripping handle 64 is placed at the most distal end of the second piston 60.

The two-chambered syringe further comprises a latching mechanism that can alternate between an unlocked configuration and a locked configuration. See generally FIGS. 3-4 and 7-8. In the locked configuration, the second piston 60 is longitudinally locked relative to the inner barrel/first piston 30. See FIG. 15(b). In this configuration, the second piston 60 will not move longitudinally relative to the inner barrel/first piston 30. See FIGS. 5 and 15(a)-15(e). However, a longitudinal force applied to the second piston 60 will be transferred proximally and the inner barrel/first piston 30 will move relative to the outer barrel 10.

In the unlocked configuration, the second piston 60 is free to move longitudinally relative to the inner barrel/first piston 30. See FIGS. 6 and 15(f)-15(g). Thus, the contents of the inner barrel/first piston 30 are ejected through the second conduit 44 when the second piston 60 is depressed. When the second piston 60 is retracted, the inner barrel/first piston 30 will provide sufficient suction to draw in the contents of the outer barrel 10 through the second conduit 44.

In one embodiment, the latching mechanism comprises a projection 68, extending outward radially from near the second piston proximal end 66. See FIGS. 1 and 3. In this embodiment, the projection is constructed of a polypropylene or other similar inert, nonreactive semi-flexible material the same as or similar to that comprising the barrels and pistons of the syringe. While the radial width of the projection 68 shown in FIGS. 1 and 3 is small relative to the distance around piston rod 62, the same principle preventing movement of the piston rod 62 would apply regardless of the radial width or shape of projection 68. See FIG. 3.

This projection fits snugly into a groove 34 cut into the inner barrel/first piston inner wall 50, thereby allowing the second piston 60 to only move according a path of movement defined by groove 34. See FIGS. 3 and 6.

The groove 34 includes a longitudinal portion 39 extending longitudinally along the inner barrel/first piston inner wall 50, ending at the inner barrel/first piston proximal end 40. See FIG. 6. Near the distal end of the inner barrel/first piston 30, the longitudinal portion 39 makes a substantially right angle and continues circumferentially around the inner barrel/first piston inner wall 50 as a radial portion 37. See FIGS. 3, 6, and 8. In one embodiment, the radial portion 37 of the groove 34 extends less than one half of one revolution of the perimeter around the inner barrel/first piston inner wall 50. See FIGS. 7 and 8.

In one embodiment, the groove 34 continues to substantially the distal end of inner barrel/first piston 30, outlining a track ultimately leading to a projection entry point 36. See FIGS. 3, 6, 7. The projection entry point 36 serves as an entrance to the groove 34 for the projection 68, simplifying the assembly process for the syringe and reducing the cost of construction. In the alternate embodiment, shown in FIG. 8, the second piston 60 with protrusion 68 would be installed into the inner barrel by applying sufficient pressure to temporarily flex the plastic allowing a press-fit construction. See FIGS. 3 and 8.

When the second piston 60 is in the fully extended position, the projection 68 will lie in the radial portion 37 of the groove 34. See FIG. 5. From this position, the second piston 60 may be axially rotated, and the projection 68 will slide along the radial portion 37 of the groove 34. Additionally, the second piston 60 and the inner barrel/first piston 30 are longitudinally locked together, and in this fixed position the two components function collectively as one piston relative to the outer barrel 10. See FIGS. 5 and 15(a)-15(e). The syringe may then be used in the same manner as a conventional one-chambered syringe, as described later herein.

In yet another embodiment, instead of comprising a track defined by an indented groove on the inner barrel/first piston 30, the syringe comprises a track defined by a raised track 35 outlining the same path previously defined by the groove 34. See FIGS. 2-4, and 16. Correspondingly, the second piston 60 comprises an indentation 69 instead of the projection 68. See FIGS. 2-4. In this configuration raised track 35 fits snugly into indentation 69, thus defining a track for the second piston 60 to follow when in the unlocked position. See FIGS. 2 and 4. In this embodiment, the track need not extend longitudinally the entire length of the inner barrel to accomplish the locking feature.

To ensure the saline does not leak backwards out of the flush chamber, the second piston 60 may additionally comprise breakaway guard 75, which provides a cover over the indentation 69. The breakaway guard 75 may be a layer of plastic that is capable of being punctured by raised track 35 when the operator applies sufficient force. The operator of the syringe will feel the resistance and subsequent release as the breakaway guard is punctured. See FIGS. 2, 4, and 16. The need for this guard may be circumvented by making a rear lip 31 large enough to prevent backward flow of the flush solution. The lip 31 of the inner barrel enables a unidirectional press fit construction (due to the sloped angle of the lip 31) in which the second plunger may be easily slid into the inner barrel, but cannot be easily removed. Thus, the second piston 60 is effectively trapped between the raised track 35 and the lip 31 thus preventing the second piston from moving longitudinally with respect to the inner barrel/first piston when the second piston is in the locked configuration. See FIGS. 15(a)-15(f).

Other latching mechanisms may be used, some of which are described further below with respect to FIGS. 22-30. For purposes of this patent, "latching mechanism" refers generically to any structure that can lock and unlock the inner barrel/first piston 30 relative to the second piston 60. See FIG. 1.

One advantage of applicant's device is that the syringe may function as a traditional syringe, independent of the internal flush chamber in the inner barrel/first piston 30. See FIGS. 15(b)-15(e). Additionally, this syringe may be used to dispense a flush solution without filling the outer chamber with a second liquid or gas.

In operation, the syringe will typically first be in the locked position so medicine withdrawn from a bottle fills the outer chamber 10. See FIG. 15(a)-(d). When medication is administered directly to a vein, a clinician using a traditional syringe will often confirm that a vein has been pierced by drawing a small amount of blood into the syringe, prior to injection of the medication. This device allows for this normal operation to be performed when the device is in the locked configuration. See FIGS. 15(b)-15(c).

Because the flushing liquid 52 does not extend through the second conduit 44, it will not mix with fluid drawn into the outer chamber 10. In a separate embodiment (shown in FIG. 5), flushing liquid 52 extends only partially through the second conduit 44, but not enough to mix with fluid drawn into outer chamber 10. The two fluids will not come in contact with each other due to basic fluid mechanics. That is, surface tension of the fluid drawn into the outer chamber 10 prevents it from entering the second conduit 44. The flushing liquid 52 does not move through the second conduit because as it completely fills the inner barrel/first piston 30, the negative pressure created inside the outer barrel 10 when fluid is drawn in, is not great enough to displace the flushing liquid 52 from the inner barrel/first piston 30.

Next, while the syringe is still in the locked configuration, the contents of the outer barrel 10 may be delivered to a patient by depressing the second piston 60. See FIGS. 15(e)-15(f). After injecting the medication, the operator may axially rotate the second piston 60 until the longitudinal portion 39 of either the groove 34 or the track 35 defines the path of movement. See FIGS. 6 and 15(f)-15(g). In the embodiments shown in FIG. 2 and FIG. 8 the clinician may confirm this alignment upon feeling that the axial rotation is halted by forward projection 67. In the embodiments shown in FIG. 1 and FIG. 3, a clinician may confirm this alignment by rotating the second piston 60 until an indicating mark on second piston 60 is longitudinally in line with a mark on the inner barrel/first piston 30 or the outer barrel 10. From this position, the second piston 60 may be longitudinally moved down the length of the inner barrel/first piston 30, thereby emptying the contents of the inner barrel/first piston 30 into the outer barrel 10 and then into the catheter. See FIGS. 6 and 15(f)-15(g).

In the embodiment shown in FIG. 2, after the outer barrel is dispensed the second plunger may be rotated axially until the forward protrusion 67 meets the raised track 35, impeding further rotation. From this position, proper alignment of the track and indentation is assured because the forward protrusion 67 is adjacent to the indentation 69. Next, the operator would depress the second piston 60 a second time, emptying the contents of the inner barrel through second conduit 44. See FIGS. 6 and 15(f)-15(g). Preferably, at this point in the process, the medication from the outer barrel 10 is already expelled into the intravenous system, and thus the contents of the inner barrel/first piston 30 may be used to flush any remaining medication into the patient.

Figure 18:
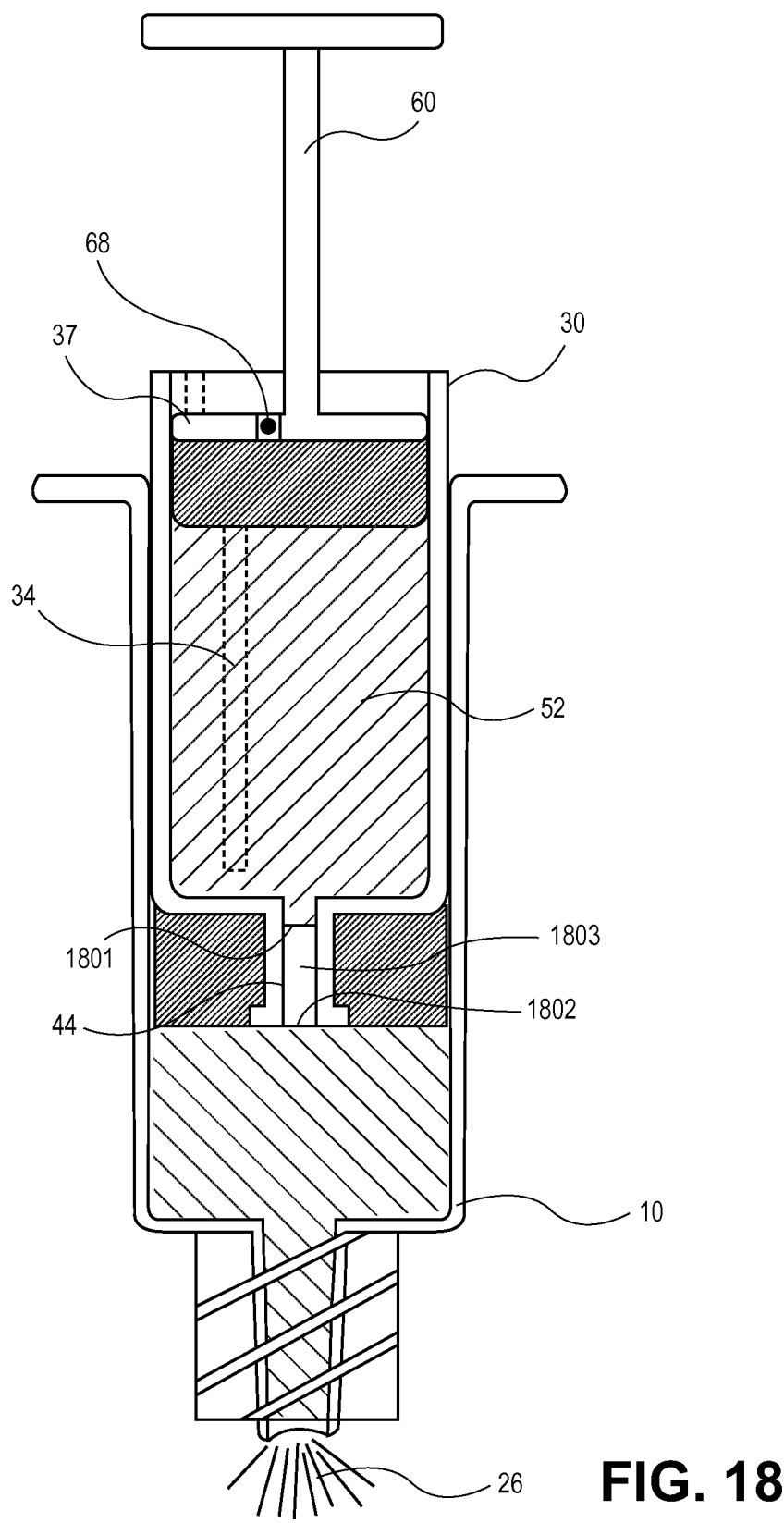
FIG. 18 is a side cross-sectional view of the embodiment depicted in FIG. 1, with the inner barrel/first piston full of a liquid such that there is a liquid-air interface at or within the conduit.

As shown in FIG. 18, and as described above, the syringe described herein includes an outer barrel 10 and an inner barrel 30 that is movable within the outer barrel 10. The inner barrel 30 has a first end which defines a conduit 44 that is in fluid communication with the outer barrel 10. The inner barrel 30 is movable within the outer barrel 10 such that the inner barrel 30 can act as a piston. A second piston 60 can be located within the inner barrel 30 so as to draw or flush fluid in or out of the inner barrel 30. The inner barrel 30, piston 60, and conduit 44 can together be called a "cartridge" of the syringe. The syringe may further include a locking mechanism on the inner barrel 30 (e.g., having groove 34 as shown in FIG. 18). The locking mechanism prevents movement of the piston 60 within the inner barrel 30 while in the locked configuration. The outer barrel 10 defines a proximal chamber and the inner barrel 30 defines a distal chamber. The proximal chamber will typically hold a medicine, while the distal chamber will typically hold a prefilled flushing liquid such as saline.

The inner barrel 30 is thus adapted to hold a liquid 52 in the distal chamber. A liquid-air interface 1801 is created within the conduit 44 which, along with the fixed volume created by the locking mechanism, prevents movement of the liquid out of the conduit 44. Further, the liquid 52 and the liquid of the outer barrel 10 will not come in contact with each other due to basic fluid mechanics. That is, the physical properties of the conduit 44 and the surface tension of the fluid drawn into the outer barrel 10 prevent the fluid from entering the second conduit 44, while the physical properties of the conduit 44 and the surface tension of the liquid 52 within the inner barrel 30 prevent the liquid 52 from exiting the inner barrel 30 through the conduit 44. Moreover, the flushing liquid 52 does not move through the conduit 44 because it completely fills the inner barrel 30, which is locked with a fixed volume. As a result, the negative pressure created inside the outer barrel 10 when fluid is drawn in is not great enough to displace the liquid 52 from the inner barrel.

After a clinician fills the outer barrel 10 with a fluid or medicine, larger air bubbles in the inner barrel 10 are removed by a standard process of tapping the side of the syringe to cause the air bubbles to coalesce into one large bubble which is expelled by orienting the syringe such that the air bubble is near the syringe tip and then the plunger is depressed to expel this air. However, the air that was originally in the conduit 44 as a result of filling of the inner barrel 30 remains in place due to the force of the surface tension and the fixed volume of the inner barrel 30. The standard process of removing the larger air bubbles does not dislodge the retained air within the conduit. When the outer barrel 10 is filled with a fluid, the distal end of the proximal chamber includes a second liquid-air interface 1802, forming a bubble or air pocket 1803 that plugs the conduit 44. The gas-filled space defined by the inner wall of the conduit 44 and the two fluid interfaces act as a plug to keep the two fluids separate until the inner barrel 30 is unlocked.

Because the liquid 52 does not extend through or extends only partially through the second conduit 44, it will not mix with fluid drawn into the outer chamber 10. That is, the bubble 1803 acts as a barrier between the fluids in the two chambers. The bubble is preferably small, having a volume of about 0.01 ml to 0.1 ml. In some embodiments, the volume is about 0.024 ml. This bubble is of substantially similar size to, or smaller than, micro bubbles which routinely form in conventional syringes used to administer medicine to patients. In fact, most conventional prefilled saline syringes contain incidental gas bubbles larger than about 0.024 ml. Clinically, small bubbles are unavoidable and completely harmless. Once injected into the patient they are broken up in the capillary bed and absorbed from the circulation without any effects to the patient. A large bubble is commonly defined as a bubble having a volume greater than 50 ml. A large bubble can behave differently from a small bubble and can be dangerous to a patient if injected into their blood stream. In contrast, the small bubble formed in the conduit 44 is not dangerous to a patient and can be beneficial for creating the valve feature, as described herein.

The bubble 1803 is held into position by forces that include surface tension, buoyancy, gravity, resistance to flow, the shape of the conduit, and the fixed volume of the cartridge chamber. Thus, the force required to dislodge the bubble depends on the dimensions of the conduit 44, the fluid viscosity and the compliance of the saline chamber. It also depends on the surface tension, contact angle of the fluid, wettability of the surface, and shape of the conduit 44. FIGS. 18A and 18B represent the balance of forces in the conduit 44 when a liquid-air interface 1810 is formed between air 1812

(e.g. the bubble 1803) and liquid 1814. The buoyancy force, Fb, is directed upward with respect to the Earth's surface. The surface tension, Fγ, is directed along the contact angle at the edge of the liquid-air interface 1810. The gravity force, Fg, is directed downward with respect to the Earth's surface. The pressure in the fluid, P1, is applied equally and perpendicular to all surfaces, including the liquid-air interface 1810 and the inner walls of the conduit 44. Likewise, the pressure in the air, P2, is applied equally to all surfaces, including the liquid-air interface 1810 and the inner walls of the conduit 44.

The syringe system is nearly rigid; the volume contained within the inner barrel 30 of the syringe is constant if the second piston 60 is fixed in position by the locking mechanism. As a result, the bubble 1803 in the conduit 44 will remain in position. When the locking mechanism is unlocked, however, and the second piston 60 is depressed, the bubble's rear surface is disrupted by the forward flow of liquid 52, causing the bubble to be propelled forward into the outer chamber 10 and/or out through the proximal outlet of the outer chamber 10.

The stability of the bubble position is related to the force of attachment to the wall of the conduit 44. This can be measured as a pressure needed to detach and move the bubble. The pressure needed to move the bubble out of the conduit is a function of the following variables: dimensions of the conduit 44, the fluid viscosity, the compliance of the inner barrel 30, the surface tension, contact angle of the fluid and wettability of the surface. These dependencies are detailed below.

In some embodiments, the conduit 44 between the proximal and distal chambers has a cylindrical shape, with radius R and length L. When the volume of the bubble is greater than that of a sphere equal to $\frac{4}{3}\pi R^3$, the bubble elongates in the conduit into a cigar shape, as shown in FIG. 18. The external force holding the bubble stationary depends on the bubble half length, H and the bubble radius, R in the following way:

$$F \propto H^2 R$$

This equation assumes that $$\frac{H^2}{R^2} > 1$$

Thus, the length of the bubble 2H is maximum when 2H is equal to L, and the resistive force of the bubble will increase more when length is increased than when radius is increased. Accordingly, the dimensions of the conduit can be chosen such that the bubble keeps the fluid in the first chamber and the fluid in the second chamber apart. In one particular embodiment, the conduit has a diameter of about 0.069 inches. In one particular embodiment, the conduit has a length of about 0.4 inches.

Viscosity is a fluid property that describes it's resistance to flow. It is also known as the 'thicknesses' of the fluid. A higher force will be required to attain the same fluid velocity for a higher viscosity fluid. The resistance of the bubble 1803 is slightly increased with increased viscosity. Most medicines will not have a viscosity difference from saline of a magnitude that would significantly affect the resistance.

The position of the bubble 1803 will also be a function of the compliance of the distal chamber (of inner barrel 30), which can be affected by the relative displacement of the locking mechanism while in the locked configuration. If the locking mechanism is not designed or built with the appropriate rigidity, excess motion (wiggle of the locking mechanism) is capable of producing a change in volume of the distal chamber, this can cause the bubble to be dislodged from the conduit 44. If the bubble can be dislodged from the conduit 44, then a small amount of mixing of the saline with the medicine may occur. The maximum displacement can be determined by the following equation:

$$\text{maximum displacement} = \frac{R}{R_{distal}} L$$

where $R_{distal}$ is the radius of the proximal chamber and R, L as defined earlier.

The compliance of the proximal chamber (of inner barrel 30) will also be influenced by the compliance of the second end of the cartridge, for example by the compliance of a rubber plunger, $C_{plunger}$, if the rubber plunger comprises part of the conduit. If the rubber plunger compresses significantly under pressure, it can reduce the proximal chamber volume and dislodge the bubble. The compressive volume change over the expected range of pressure should be less than an amount equal to the current conduit 44 volume.

$$\Delta V = \Delta P \cdot C_{plunger} < \pi R^2 L$$

The surface tension of a fluid is a measure of how readily the fluid surface is attracted to another surface. It is a property of a fluid that is related to the surface free energy, and affects the contact angle. The force or pressure needed to dislodge the bubble 1803 from the conduit 44 is increased with increasing surface tension.

Contact angle is classically measured by placing a drop on a horizontal surface and measuring the angle of the drop edge. The contact angle is determined from the position of the interfaces between solid, liquid and gas at equilibrium. If a droplet of water spreads on a solid surface, the contact angle is very small and the surface is considered hydrophilic. If the droplet rounds up, the contact angle is greater than 90°, and the surface is hydrophobic. The contact angle of the fluid used is preferably less than 90° to maintain the bubble seal between the two chambers.

The wettability of a surface is directly related to the contact angle, and is another indication of the balance of forces within the liquid that are cohesive, and those between the liquid and the surface that are adhesive. A hydrophilic contact angle is indicative of a strong attraction between the fluid and the surface, a surface that is considered wetting.

Once a caregiver receives a syringe having a prefilled distal chamber, filling the proximal chamber (of the outer barrel 10) follows the standard operation for filling a syringe, which includes the steps of (1) fitting a syringe with a needle (metal or plastic) to penetrate the seal on a medicine bottle; (2) pulling the handle of the syringe back (distally) to draw air into the syringe of equal or greater volume than the medicine that is to be withdrawn; (3) inserting the air filled syringe with attached needle into the medicine bottle; (4) depressing (pushing proximally) the plunger to inject the air into the medicine bottle; (5) pulling the handle of the syringe back (distally) to draw medicine from the bottle into the syringe; and (6) withdrawing the needle/syringe from the medicine bottle and removing the needle from the syringe.

The syringe may then be connected to the patient or patient line at a luer port for injection of the medicine. The handle is depressed to inject the medicine, then the cartridge is unlocked and the handle depressed further to inject the saline. The syringe is removed and discarded.

In general, a method of using a syringe includes the steps of drawing a second liquid (such as medicine) into the outer barrel 10 through the proximal outlet by moving the inner barrel 30 distally within the outer barrel 10 and creating a second liquid-air interface within the conduit. As described above, the second liquid-air interface and the first liquid-air interface define a bubble which, cooperating with the conduit 44, prevent movement of the first liquid out of the conduit 44 and prevent movement of the second liquid into the conduit 44. In some embodiments, the method further includes the steps of (a) expelling the second liquid (such as medicine) from the outer barrel 10 through the proximal outlet by moving the inner barrel 30 proximally within the outer barrel 10, (b) releasing the locking mechanism from a locked configuration to an unlocked configuration to allow movement of the piston 60 within the inner barrel 30, and (c) expelling the first liquid (such as saline) from the inner barrel of the cartridge through the proximal outlet by moving the piston 60 proximally within the inner barrel 30. In some embodiments, the step (c) of expelling the first liquid includes expelling the gas bubble from the conduit, along with the first liquid, through the proximal outlet. As described above, the gas bubble within the conduit disposed between the first liquid-gas interface and the second liquid-gas interface is a small bubble, safe for injection into a patient.

Figure 19A:
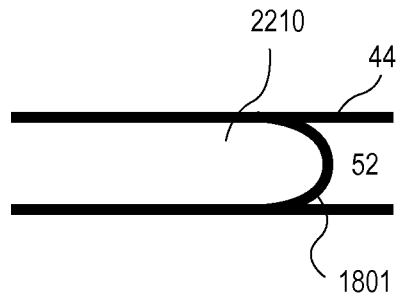
FIGS. 19A-19H illustrate multiple embodiments of the shape of a bubble in the conduit of a syringe.

The different stages of use described above will have varying effects on the bubble 1803 formed in the conduit 44. FIG. 19A represents the shape of the air pocket 2110 in the conduit 44 during shipping. As shown, only one liquid-air interface 1801 will be present, as no medicine or additional fluid will have been added to the proximal chamber.

Figure 19B:
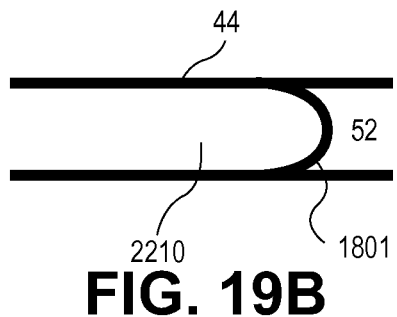

FIG. 19B represents the shape of the air pocket 2110 in the conduit 44 when the proximal chamber is filled with air prior to ejecting the air into the bottle containing fluid (for later uptake of fluid into the proximal chamber). Although there is a slight negative pressure created in the proximal chamber as air is draw in from the open atmosphere, the effect is negligible, and the shape of the liquid-air interface 1801 remains substantially unchanged.

Figure 19C:
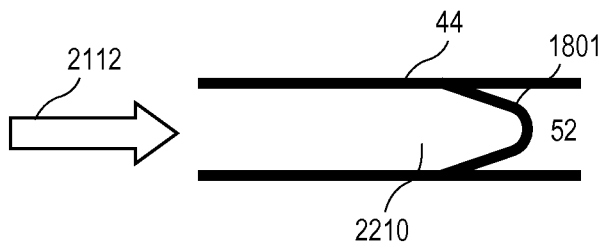

FIG. 19C represents the shape of the air pocket 2210 during injection of air into the bottle. The arrow 2112 shows the net direction of force on the air pocket 2210 resulting from pressure generated as the proximal chamber is depressed. There is a distal deformation of the liquid-air interface 1803 resulting from the force.

Figure 19D:
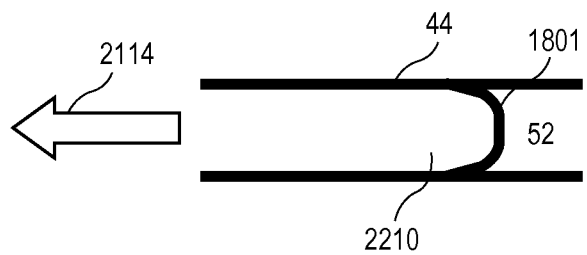

FIG. 19D represents the shape of the air pocket 2210 during withdrawal of medication into the proximal chamber from the bottle. The arrow 2114 shows the net direction of force on the air pocket 2210. The negative pressure in the proximal chamber causes a proximal deformation of the liquid-air interface 1801 without disrupting the liquid-air interface 1801.

Figure 19E:
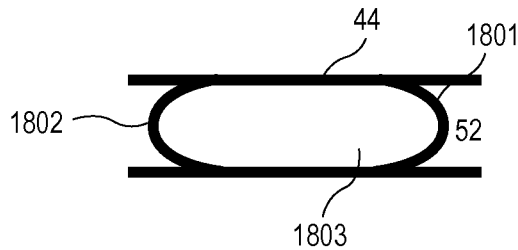

FIG. 19E represents the air bubble 1803 formed after fluid has been filled into the proximal chamber. A net zero force is on the bubble 1803 such that the liquid-air interface 1802 formed near the proximal chamber has the same curvature in the opposite direction as the liquid-air interface 1801 formed near the distal chamber.

Figure 19F:
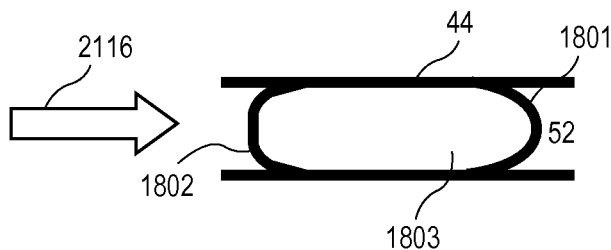

FIG. 19F represents the shape of the air bubble 1803 as the fluid from the proximal chamber is administered to the patient. As the fluid is released, the bubble 1803 experiences a net distal force as a result of the pressure in the proximal chamber, represented by the arrow 2116. As a result, both the liquid-air interface 1802 near the proximal chamber and the liquid-air interface 1801 near the distal chamber move distally.

Figure 19G:
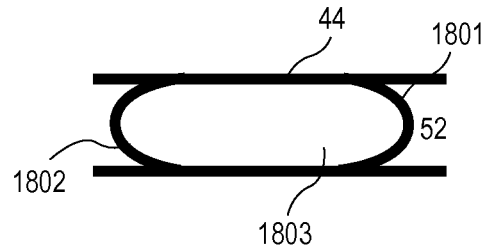

FIG. 19G represents the shape of the air bubble 1803 after the contents have been dispensed from the proximal chamber. Due to the surface tension of the bubble, a small amount of liquid remains in conduit on the proximal side of the bubble 1803. As a result, the liquid-air interface 1802 on the proximal side remains intact.

Figure 19H:
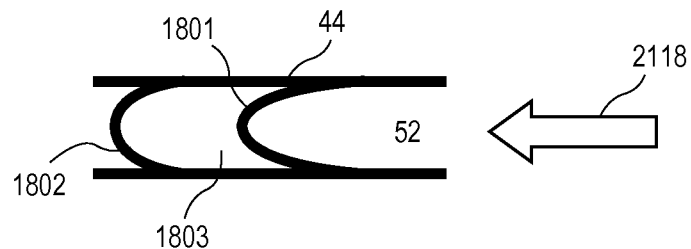

FIG. 19H represents the shape of the bubble 1803 as the fluid 52 in the distal chamber is expelled. The net direction of force on the bubble 1803 is proximal, as shown by arrow 2118. As the solution 52 is discharged, there is initial proximal deformation of both the liquid-air interface 1802 on the proximal side as well as the liquid-air interface 1803 on the distal side. The force 2118 is great enough in the proximal direction that the bubble 1803 will eventually be displaced.

One skilled in the art will appreciate that the present invention can be practiced by other than the preferred embodiments, which are presented for purposes of illustration and not of limitation.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A syringe comprising:
   a cartridge comprising:
      a first chamber,
      a first end having a conduit in liquid communication with the first chamber,
      a liquid disposed within the first chamber, wherein the conduit is adapted and configured to rely on a property of the liquid to prevent movement of the liquid out of the first chamber,
      a second end, movable within the first chamber, and
      a locking mechanism having a locked configuration and an unlocked configuration, the locking mechanism being adapted to prevent movement of the second end within the first chamber while in the locked configuration;
   a second chamber having a second liquid disposed therein, wherein the cartridge is movable within the second chamber; and
   a gas bubble disposed in the conduit between the first liquid and the second liquid.

2. The syringe of claim 1, wherein the conduit is adapted and configured to rely on a property of the liquid to cause a liquid-air interface to form in the conduit that prevents movement of the liquid out of the first chamber.

3. The syringe of claim 1, wherein the conduit is further adapted and configured to rely on a property of the second liquid to prevent movement of the second liquid into the first chamber.

4. The syringe of claim 1, wherein the gas bubble has a volume that can readily dissolve into solution when injected into a patient.

5. The syringe of claim 1, wherein the cartridge comprises 1 to 10 ml of liquid disposed within the first chamber.

6. The syringe of claim 1, wherein the cartridge comprises 2 to 3 ml of liquid disposed within the first chamber.

7. The syringe of claim 1, wherein a volume of the first chamber is constant while the locking mechanism is in the locked configuration.

8. The syringe of claim 1, wherein the conduit comprises a surface finish that contributes to preventing movement of the liquid out of the first chamber.

9. The syringe of claim 1, wherein the dimensions of the conduit contribute to preventing movement of the liquid out of the first chamber.

10. The syringe of claim 1, wherein the conduit has a diameter of 0.069 inches.

11. The syringe of claim 1, wherein the conduit has a length of 0.4 inches.

12. The syringe of claim 1, wherein the second end of the cartridge further comprises a handle sized and configured to move the second end within the first chamber when the locking mechanism is in the unlocked configuration.

13. The syringe of claim 12, wherein the handle is configured to move the cartridge within the second chamber when the locking mechanism is in the locked configuration.

* * * * *